US00PP15372P2

(12) United States Plant Patent
Jepsen

(10) Patent No.: US PP15,372 P2
(45) Date of Patent: Nov. 23, 2004

(54) *KALANCHOE* PLANT NAMED 'KJ 2002-0500'

(50) Latin Name: *Kalanchoe blossfeldiana*
Varietal Denomination: KJ 2002-0500

(75) Inventor: Knud Jepsen, De Kwakel (NL)

(73) Assignee: Knud Jepsen A/S, Hinnerup (DK)

( * ) Notice: Subject to any disclaimer, the term of this patent is extended or adjusted under 35 U.S.C. 154(b) by 0 days.

(21) Appl. No.: 10/654,569

(22) Filed: Sep. 2, 2003

(51) Int. Cl.[7] ..... A01H 5/00
(52) U.S. Cl. ..... Plt./341
(58) Field of Search ..... Plt./341

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of *Kalanchoe* plant named 'KJ 2002-0500', characterized by its upright plant habit; dark green-colored leaves; large red-colored flowers with more than 15 petals per flower; and excellent postproduction longevity.

1 Drawing Sheet

Botanical classification/cultivar designation: *Kalanchoe blossfeldiana* cultivar KJ 2002-0500.

BACKGROUND OF THE INVENTION

The present invention relates to a new and distinct cultivar of *Kalanchoe* plant, botanically known as *Kalanchoe blossfeldiana*, and hereinafter referred to by the name 'KJ 2002-0500'.

The new *Kalanchoe* is a product of a planned breeding program conducted by the Inventor in Hinnerup, Denmark. The objective of the breeding program was to create new freely-flowering *Kalanchoe* cultivars with large flowers, numerous petals per flower, attractive flower coloration and excellent postproduction longevity.

The new *Kalanchoe* originated from a cross-pollination made in Hinnerup, Denmark, of the *Kalanchoe* cultivar Molly, disclosed in U.S. Plant Pat. No. 12,307, as the female, or seed, parent with the *Kalanchoe* cultivar 2001-1855, not patented, as the male, or pollen, parent. The new *Kalanchoe* was discovered and selected by the Inventor as a single flowering plant with the progeny of the stated cross-pollination grown in a controlled environment in Hinnerup, Denmark.

Asexual reproduction of the new *Kalanchoe* by terminal cuttings taken at Hinnerup, Denmark, by the Inventor, has shown that the unique features of this new *Kalanchoe* are stable and reproduced true to type in successive generations.

BRIEF SUMMARY OF THE INVENTION

The cultivar KJ 2002-0500 has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'KJ 2002-0500'. These characteristics in combination distinguish 'KJ 2002-0500' as a new and distinct cultivar:

1. Upright plant habit.
2. Dark green-colored leaves.
3. Large red-colored flowers with more than 15 petals per flower.
4. Excellent postproduction longevity.

Plants of the new *Kalanchoe* differ from plants of the parent cultivars in petal number and coloration.

BRIEF DESCRIPTION OF THE PHOTOGRAPHS

The accompanying colored photographs illustrate the overall appearance of the new *Kalanchoe*, showing the colors as true as it is reasonably possible to obtain in colored reproductions of this type. Colors in the photographs may differ slightly from the color values cited in the detailed botanical description which accurately describe the colors of the new *Kalanchoe*. The photographs were taken under diffuse natural light conditions on a sunny day at approximately noon in Hinnerup, Denmark.

The photograph at the top of the sheet comprises a side perspective view of a typical potted plant of 'KJ 2002-0500'.

The photograph at the bottom of the sheet comprises a top perspective view of a typical plant of 'KJ 2002-0500'.

DETAILED BOTANICAL DESCRIPTION

In the following description, color references are made to The Royal Horticultural Society Colour Chart, 1995 Edition, except where general terms of ordinary dictionary significance are used. Plants used in the photographs and for the following observations and measurements were grown in Hinnerup, Denmark, under commercial practice in a glass-covered greenhouse for about 10 weeks after the start of short day/long night photoperiodic treatment with average temperatures of 20° C. Plants used in the description and photographs were not pinched. Unless otherwise specified, the leaf description represents leaves from a vegetative plant.

Botanical classification: *Kalanchoe blossfeldiana* cultivar KJ 2002-0500.

Parentage:

Female, or seed, parent.—*Kalanchoe blossfeldiana* cultivar Molly, disclosed in U.S. Plant Pat. No. 12,307.

Male, or pollen, parent.—*Kalanchoe blossfeldiana* cultivar 2001-1855, not patented.

Propagation:

*Type cutting.*—Terminal cuttings.

*Time to produce a rooted young plant.*—About 14 days.

*Root description.*—Numerous, fine, fibrous, and well-branched.

Plant description:

*Form.*—Upright plant habit with numerous compound cymes; freely flowering. Actual plant shape will depend on whether or not plants are pinched (apical terminals removed).

*Branching habit.*—Freely branching. Pinching (removal of terminal apex) is not required but will enhance lateral branch development.

*Plant height at flowering.*—About 26 cm.

*Plant diameter at flowering.*—About 20 cm.

*Foliage description.*—Arrangement: Opposite, simple. Size: Leaf size is reduced after floral induction. Vegetative plants: Length: About 9 cm. Width: About 6 cm. Reproductive plants: Length: About 5 cm. Width: About 3 cm. Shape: Oval. Apex: Obtuse. Base: Obtuse. Margin: Crenate; undulate. Aspect: Slightly concave. Texture: Glabrous; leathery; succulent. Color: Developing and fully expanded foliage, upper surface: 147A. Developing and fully expanded foliage, lower surface: 147B.

Flower description:

*Flower type and habit.*—Single flowers arranged in compound dichasial cymes that arise from leaf axils. Upright flowering stems. Freely flowering. Flowers persistent.

*Natural flowering season.*—Winter to early spring; flower initiation and development can be induced under short day/long night conditions.

*Time to flower.*—In the summer with 20° C. growing temperatures, about ten weeks of short day/long night conditions are required to produce flowering plants. During the winter the supplemental lighting and 20° C. growing temperatures, about eleven weeks of short day/long night conditions are required to produce flowering plants. Time to flower is primarily dependent upon temperature and light intensity.

*Flower opening.*—First flower open is the terminal flower at the main axis and is followed by the opening of the terminal flowers of the side branches of the inflorescence. About one week after the first flower has opened, 50% of the remaining flowers are open.

*Post-production longevity.*—Plants of the new *Kalanchoe* maintain good leaf and flower substance for at least five weeks under interior environmental conditions.

*Flower diameter.*—About 2.4 cm.

*Quantity.*—Freely flowering, at least 150 flowers per plant.

*Flower buds.*—Shape: Narrowly oblong. Length: About 1.6 cm. Width: About 6 mm. Color: 63A.

*Petals.*—Quantity: Typically more than 15 fused at base. Length: About 1 cm. Diameter: About 5 mm. Shape: Round obovate. Apex: Cuspidate. Margin: Entire. Texture: Glabrous, smooth and satiny. Color: Upper surface: 46A; color becoming closer to 60A with development. Lower surface: 66C.

*Reproductive organs.*—Stamens: Stamen number: At least 15. Anther shape: Slightly oblong. Filament color: Green. Pollen color: Yellow. Pistils: Pistil number: About eight to ten. Style color: Green. Stigma shape: Round. Ovaries: Superior and four-celled. Ovary size: About 1.6 cm by 1 mm. Ovary color: Light green.

*Seed/fruit.*—Seed and fruit production has not been observed.

Disease/pest resistance: Resistance to known pathogens and pests common to *Kalanchoe* has not been observed on plants of the new *Kalanchoe* grown under commercial greenhouse conditions.

It is claimed:

1. A new and distinct cultivar of *Kalanchoe* plant named 'KJ 2002-0500', as illustrated and described.

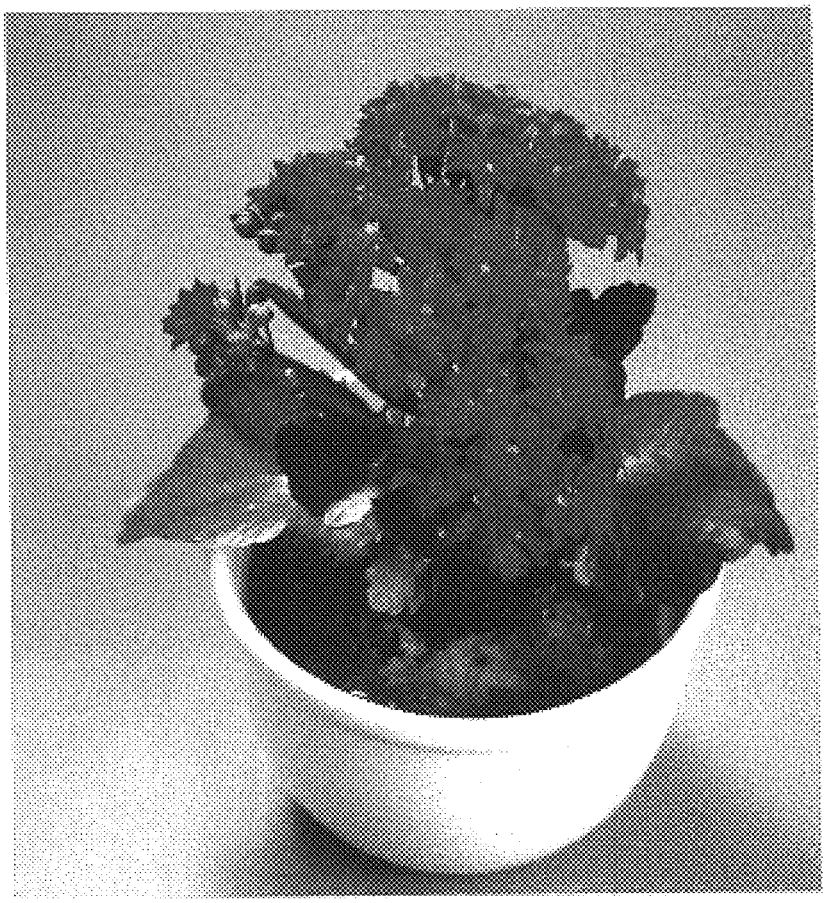
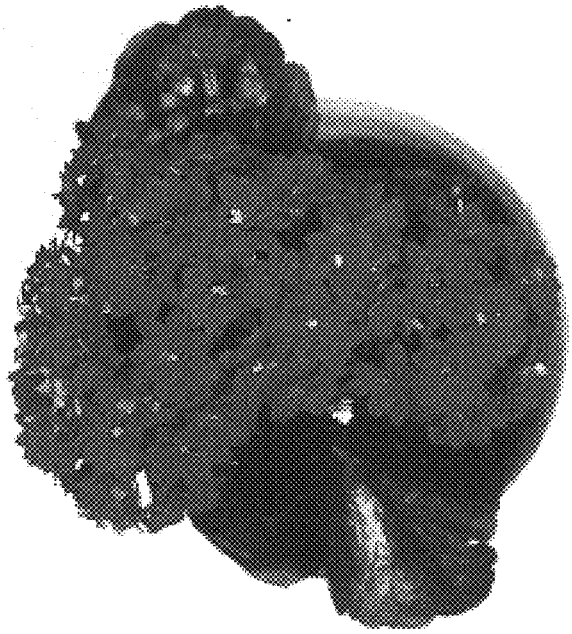

* * * * *